(12) United States Patent
Figueras et al.

(10) Patent No.: US 7,060,859 B2
(45) Date of Patent: Jun. 13, 2006

(54) USE OF A SOLID HYDROTALCITE STRUCTURE INCORPORATING FLUORIDES FOR BASIC CATALYSIS OF MICHAEL OR KNOEVENAGEL REACTIONS

(75) Inventors: Francois Figueras, Lyons (FR); Boyapati Manoranjan Choudary, Hyderabad (IN); Mannepalli Lakshmi Kantam, Hyderabad (IN); Vattipally Neeraja, Secunderabad (IN); Kottapalli Koteswara Rao, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/144,594

(22) Filed: Jun. 6, 2005

(65) Prior Publication Data

US 2005/0250963 A1 Nov. 10, 2005

Related U.S. Application Data

(63) Continuation of application No. 10/220,952, filed as application No. PCT/FR01/00670 on Mar. 6, 2001.

(30) Foreign Application Priority Data

Mar. 8, 2000 (FR) .................................. 00 02987

(51) Int. Cl.
*C07C 45/00* (2006.01)
*C07C 209/00* (2006.01)
*C07C 69/00* (2006.01)
*C07C 255/00* (2006.01)

(52) U.S. Cl. ...................... 568/312; 568/315; 568/316; 568/347; 568/348; 568/391; 568/393; 564/469; 560/115; 560/128; 560/174; 558/357; 558/365; 558/371

(58) Field of Classification Search ................ 568/312, 568/315, 316, 347, 348, 391, 393; 558/357, 558/365, 371; 560/115, 128, 174; 564/469
See application file for complete search history.

(56) References Cited

U.S. PATENT DOCUMENTS

| 4,458,026 A | 7/1984 | Reichle |
| 5,260,495 A | 11/1993 | Forkner |
| 6,686,498 B1* | 2/2004 | Jacoby ....................... 560/174 |
| 6,812,186 B1* | 11/2004 | Choudary et al. .......... 502/150 |

FOREIGN PATENT DOCUMENTS

WO   WO 98/51615 A   11/1998

OTHER PUBLICATIONS

Choudary et al. The first example of Michael addition catalysed by modified Mg-Al hydrotalcite.□□Jounal of Molecular Catalysis A: Chemical 146 (1999) p. 279-284.*
De Roy, Andre et al., "Anionic Clays: Trends in Pillaring Chemistry", *Synthesis of Microporous Materials*, vol. II, 1992, pp. 108-169, XP000965437.
Parker, L. M. et al., "The Use of Hydrotalcite as an Anion Absorbent", *Industrial & Engineering Chemistry Research*, vol. 34, No. 4, Apr. 1, 1995, pp. 1196-1202, XP000494847.
Rousselot, I et al., "Synthesis and Characterization of Mixed Ga/A1-Containing Layered Double Hydrozides: Study of Their Basic Properties Through the Knoevenagel Condensation of Benzaldehyde and Ethyl Cyanoacetate, and Comparison to other LDSs", *International Journal of Inorganic Materials*, vol. 1, No. 2, 1999, pp. 165-174, XP000964856.
Miyata, Shigeo, "Anion-Exchange Properties of Hydrotalcite-Like Compounds", *Clays and Clay Minerals*, vol. 31, No. 4, 1983, pp. 305-311, XP000964988.

* cited by examiner

*Primary Examiner*—Sikarl A. Witherspoon
(74) *Attorney, Agent, or Firm*—Foley & Lardner LLP

(57) ABSTRACT

The invention concerns the use of a solid basic catalyst comprising a hydrotalcite structure wherein part at least of the compensating anions are fluoride anions $F^-$ for producing Knoevenagel of Michael condensation reactions. The invention also concerns novel solid basic catalysts comprising a hydrotalcite structure characterized by a Mg/Al molar ratio ranging between 2.5 and 3.8 wherein at least part of the compensating anions are fluoride anions $F^-$, and methods for preparing said novel catalysts.

7 Claims, No Drawings

USE OF A SOLID HYDROTALCITE STRUCTURE INCORPORATING FLUORIDES FOR BASIC CATALYSIS OF MICHAEL OR KNOEVENAGEL REACTIONS

This application is a continuation application of U.S. patent application Ser. No. 10/220,952, filed Mar. 24, 2003, which is the national stage application filed under 35 U.S.C. § 371 of International Application No. PCT/FR01/00670, filed Mar. 6, 2001, which claims priority from French Application No. 00/02987, filed Mar. 8, 2000.

The present invention concerns basic catalysis reactions in organic chemistry.

In organic chemistry there exist a number of reactions, which require the use of basic catalysts. For instance one can quote saponification, transesterification, epoxydation, aldolation and cetolisation reactions, Michael reactions and also the Knoevenagel condensation reactions.

On this subject one may refer to Advanced Organic Chemistry, Reactions, Mechanisms and Structures by J. March, $3^{rd}$ edition, Wiley (1985).

The basic catalysts most often used in these reactions are typically strong liquid bases such as, for example, hydroxide, hydride and metallic alkoxide solutions used for homogeneous catalysis.

In case the efficiency of these catalysts is not to be proven, these compounds too, nevertheless, have a considerable disadvantage: their use on an industrial scale produces significant amounts of saline waste water which, because of their impact on the environment, requires further treatment leading to high operational costs.

In order to avoid this problem, a great deal of effort has been made in the past years to try and replace the usual basic liquid catalysts by solid catalysts which offer the advantage of not leading to salts forming as stated above.

The first type of basic liquid catalysts suggested are a saturated solid support which includes microporous zeolites saturated by alkaline solutions, described amongst others by Hattaway et al. in the Journal of Catalysis, volume 119, page 497 (1982) or by Lasperas et al. in Microporous Materials, volume 1, page 343 (1993); alumina type supports saturated by potassium fluoride solutions (see also Clark et al., Chemical Review, volume 80, page 429 (1980) or by potassium nitrate solutions (refer to, for instance, Yamaguchi et al., Chemical letters, page 989 (1997)).

As regards heterogeneous solid catalysts, one of the important parameters to be mastered is that of porosity of solids involved. The pore size of solids used must be large enough to avoid heterogeneous catalysis inhibition linked to diffusion phenomena of species at the catalyst's surface.

Once this parameter is mastered, the saturated catalysts become interesting and efficient. The use of these catalysts not only avoids salt formation as described earlier but also has the following advantages:

During reaction, the reactor's corrosion due to the presence of the acidic compound reduces owing to the localisation of alkalinity on the solid which improves safety conditions;

At the end of the reaction, the separation of the product and the catalyst takes place easily and which also results in lower operational costs.

However, it must be noted that the immobilisation of a liquid base on a support is not a very satisfactory solution: the saturated solid catalysts have the disadvantage of gradually deactivating as they are being used because of the dissolution of the active basic compound over time. This gradual dissolution may also take place due to the presence of reaction sub-products such as water and alcohol.

In order to avoid this problem raised by the dissolution of the active compound and the loss of activity over time one has more recently opted for the use of solid compounds with higher porosity, which possess inherent strong basic properties.

In this field one has shown special interest in specific solids usually known by the generic term "activated hydrotalcite".

In a stricter sense, by "hydrotalcite" one means magnesium and aluminum hydrate basic carbonate ($Mg_6Al_2(OH)_{16}CO_3$; $4H_2O$ as described by Manasse et al. in Atti.Soc. Toscana Sc. Nat. Proc. Verb. Volume 24, page 92 (1915).

In a larger sense, the term "hydrotalcite" designates a mixed carbonatized hydroxide demonstrating a lamellar structure with thin laminae similar to those of clay. The basic structure of this solid, called hydrotalcite structure" is that of magnesium hydroxide Mg (OH) 2 wherein some of the $Mg^{2+}$cations are replaced by $Al^{3+}$cations possessing a molar ratio Mg/Al usually ranging from 1.5 to 4 and preferably to the order of 3. In this structure, an excess of charge due to the presence of $Al^{3+}$ions is neutralised by the carbonate anions $CO_3^{2-}$, which play the role of compensating anions.

It must be noted that a hydrotalcite structure cannot show a molar ratio Mg/Al higher than 4. One can, however, obtain solids with a hydrotalcite structure and possessing a global molar ratio Mg/Al higher than 4. These solids are actually mixed solids with a hydrotalcite phase and a magnesium basic carbonate phase. The synthesis of this particular carbonatized mixed hydroxide has been described by Miyata et al. in Clays and Clay Minerals, volume 23, pages 369–375 (1975) and by Reichle et al. in Journal of Catalysis, volume 94, pages 547–557 (1985).

Even though this compound possesses a marked acidic characteristic it is not of real interest to the field of applications in basic catalysis. On the other hand, some its derivatives called "activated hydrotalcites" do possess interesting basic catalysis properties.

By "activated hydrotalcite" one means, in relevance to the present invention, a compound obtained from physical, chemical and physicochemical treatment of hydrotalcite, possessing better catalysis properties to those of the initial hydrotalcite.

For instance, a mixed magnesium and aluminum oxide called "HDT" is obtained by thermal decarbonation of hydrotalcite. It has been described as an acceptable basic catalyst for aldolation reactions (refer to, for example, to the article by Suzuki et al. in the Bulletin of the Chemical Society of Japan, volume 61, pages 1008–1010 (1988)), for transesterification (refer to the Spanish patent SF 9601087 or to Corma et al.'s article in the Journal of Catalysis, volume 173, pages 315–321 (1998)), for Knoevenagel condensation reactions (see article by Climent et al. in the Journal of Catalysis, volume 151, pages 60–66 (1995)).

However, it must be noted that this mixed oxide's catalytic activity remains relatively weak.

In order to improve the catalytic qualities of this compound, it was suggested in the French patent FR 9500094, to hydrate this mixed oxide "HDT" which results in an aluminum and magnesium mixed hydroxide called "HDT-OH".

This mixed hydroxide "HDT-OH" is a Bronsted solid base with very interesting basic catalysis properties. Its use for aldolation of acetone has been described (refer to Catalysis of Organic Reactions by de Figueras et al., F. E. Herkes Edition, Marcel Dekker Inc., New York (1998), and for Knoevenagel condensations and Michael reactions (refer to article by Lakshmi Kantam et al., in Chemical Communications, volume 39, pages 1033–1034 (1998)).

One must emphasize the fact that the "HDT-OH" catalyst thus obtained is an activated hydrotalcite with a basic structure of a hydrotalcite, wherein the carbonate compensating anions $CO_3^{2-}$ have been replaced by hydroxide anions OH.

Thus, OH ions present in the "HDT-OH" structure demonstrate an important unstable characteristic. In other words, exchangeable ions.

Therefore, it must be noted that even a trace presence of chloride ions poisons this type of catalyst. The exchange of OH ions by chloride ions within a hydrotalcite structure leads, in the presence of aluminum, to strong acids forming which inhibit the catalyst's strong basic character.

However, the inventors have now discovered that if chloride ions inhibit the basic catalyst's activity of hydrotalcite-like compounds, introducing fluoride ions as compensation ions in a hydrotalcite structure leads surprisingly to a net increase in the resulting compound's basic character. This improves basic catalyst properties.

On the basis of this discovery, one of the objectives of this invention is to achieve heterogeneous basic catalysis of a Knoevenagel or Michael reaction with interesting yields.

The invention also has the intention of identifying activated hydrotalcite-like new solid basic catalysts that have a significant intrinsic basic character and which can replace advantageously the basic catalysts described in prior art.

Therefore, at first, the objective of the present invention is the use of a solid basic catalyst with a hydrotalcite structure within which, at least a part of compensation anions are comprised of fluoride anions F for the basic catalysis of a Knoevenagel and Michael reaction.

According to the invention the hydrotalcite structure of useful catalysts generally has a molar ratio Mg/Al ranging from 1.6 to 3.8.

Appropriately, according to the invention, the molar ratio Mg/Al characterising the hydrotalcite structure of useful catalysts is higher than 2, and preferably higher than 2.5. What is even better is that this ratio is higher than 2.6. Besides this molar ratio is less than 3.3. Thus, this ratio ranges between 2.5 and 3.8, preferably between 2.6 and 3.2 and most advantageously between 2.8 and 3.1. The ratio especially preferable would be 3.

The solid basic catalysts used in the invention with a hydrotalcite structure characterised specifically by a molar ratio Mg/Al between 2.5 and 3:8 and wherein at least a part of compensation anions are fluoride anions are new catalysts. These are part of another objective of the present invention.

Whatever may be the value of the hydrotalcite structure's ratio Mg/Al one must emphasize that in the catalyst considered useful by the invention, the fluoride anions are specifically integrated to the compensation ions' state in the hydrotalcite structure. They are not supported simply by a solid support, as is the case of KF type saturated catalysts supported by alumina as described earlier.

This characteristic of the catalyst can be highlighted on fluorine Nuclear Magnetic Resonance spectrum. Here one can clearly notice the fluorine present in the solid in a fluoride ion state in a totally different environment, for instance, that of pure KF or alumina supported KF.

Because of this selectivity/specificity and the similarity with the nomenclature used to designate mixed hydroxides "HDT-OH" as mentioned above, the activated hydrotalcite of useful catalysts as per the invention will be designated below by the generic term—"HDT-F". This in order to remind us that fluoride ion is present as compensation anions within the hydrotalcite structure.

However, it must be noted that bordering on the fluoride anions integrated into the activated hydrotalcite as compensation anions, the catalyst can moreover subsequently present a very small quantity of fluoride anions supported simply by the solid's surface.

In the most general of cases, the useful catalysts according to the invention preferably contain at least 0.5% as masse and advantageously at least 2.5% of fluoride ion masse. Whatever may be the content of fluoride ions, at least 95% preferably and at least 98% advantageously of fluoride ions present must be integrated to the compensation anion state within the "HDT-F" structure.

Besides in order to avoid problems linked to the relatively cumbersome diffusion of species found in organic chemistry at the solid catalyst's surface, the catalysts useful according to the invention are advantageously found in the form of porous solids. Their pore radius distribution is such that at least 50% of the pores have a mean diameter greater than 2 nm and preferably greater than 5 nm.

Herein, it must be noted that it is the specific use of an activated hydrotalcite-like compound which makes it possible to obtain solids liable to present such a high porosity level. For the sake of comparison, the modified zeolites described earlier only have pore diameters of 0.8 nm maximum.

One of the advantages of the present invention is therefore to allow reactions involving more cumbersome solid support/substrata than those used with state-of-the-art basic catalysts.

Due to their special chemical structure and high porosity, the "HDT-F" catalysts useful according to the present invention behave like normal basic catalysts; for instance, like those with a strong hydroxide or hydride type base.

In particular it has been established that the inventions' catalysts bear excellent catalysis results in two interesting reactions in organic chemistry which are the Knoevenagel and Michael reactions.

One must remember that the Knoevenagel condensation corresponds to the reaction of an aldehyde or a ketone on a compound possessing an activated methanol grouping which can be reflected in a schematic diagram by a global budget/balance:

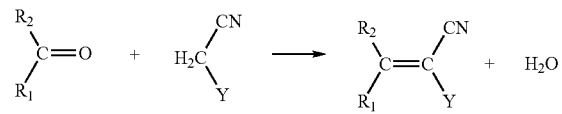

As regards the Michael reaction, it is a condensation reaction which corresponds to the following reactional schematic diagram:

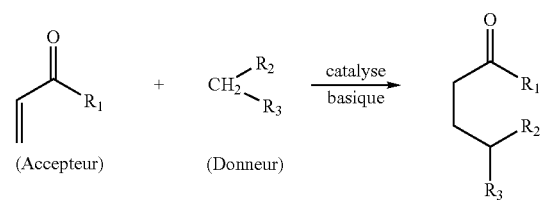

For more details on these reactions one can refer to Advanced Organic Chemistry, Reactions, Mechanisms and Structures, by J. March, $3^{rd}$ edition, Wiley (1985).

The inventors have now discovered that these reactions which are greatly used in organic chemistry for creating carbon-carbon linkage and to increase the length of carbon chains, are catalysed with excellent yields and in a very short period of time by "HDT-F" catalysts.

As a general rule, one does obtain yields higher than 80% with the invention's catalyst for periods of a reaction time of a few minutes to some hours.

In the most general cases the invention's catalysts are advantageously put to use to 0.01 g to 0.10 g per solid support/substrate millimole in order to obtain such yields.

This point must be emphasised especially with regard to Michael reaction that the productivity of catalysts of the invention may be very favourably compared with other better solid catalysts proposed earlier.

Thus, Sinistierra et al. in Synthesis, page 1037: 1041 (1982) describe for Ba(OH)2 a productivity of 50 mmol per gram of catalyst and per hour for chalcone condensation with ethylacetoacetate: whereas the productivity of the invention's catalyst amounts to 200 mmol/g/h for this reaction. Similarly. Bergbreiter et al. in the Journal of Organic Chemistry, volume 52, pages 1601–1603 (1987) gives a KF productivity supported on 1 mmol/g/h of alumina for nitroethane and cyclohexanone condensation whereas this productivity achieves 180 mmol/g/h for the invention's "HDT-F" catalyst.

Moreover, the invention's catalysts, because of their solid character can also be easily separated from products obtained at the end of the reaction. However, what is important to note is given that the fluoride anions playing the role of compensation anions are sufficiently strongly linked to the solid's structure, the 'HDT-F' catalysts mostly possess enough stability to be recycled. This is an undoubted advantage vis a vis most other solid catalysts which have been described earlier.

Thus, in the case of the Knoevenagel reaction one has observed that recycling the 'HDT-F' catalyst may be carried out at least five times without a noticeable fall in efficiency or productivity.

The 'HDT-F' basic catalyst useful according to this invention and the solid basic catalysts in particular showing a hydrotalcite structure characterised by a Mg/Al ratio between 2.5 and 3.8 may be obtained by means of two main kinds of procedure.

One method for preparing a solid basic catalyst with a hydotalcite structure integrating fluoride anions as compensation anions, useful according to the invention, is characterised by stages which:

(1.1) Prepare a solid with hydrotalcite structure; and (1.2) Subject the solid obtained at the end of stage (1.1) to an exchange reaction by fluoride ions.

The hydrotalcite structure solid of stage (1.1) may be obtained by any means known to person skilled in this art. However, to the extent that it is specifically meant for an exchange stage by fluoride ions, the hydrotalcite structure solid prepared during stage (1.1) is preferably a hydrotalcite structure compound where compensation anions are monovalent anions and preferably nitrate anions.

The considerable affinity of divalent anions for the hydrotalcite structure makes the later stage of anionic exchange difficult or next to impossible. This disadvantage is particularly clear when carbonate anions are present as compensation anions. The nitrates, on the other hand, show lesser affinity vis a vis the hydrotalcite structure. One may refer to, in particular, the article by Miyata et al. in Clays and Clay Minerals, volume 31, page 305 (1981).

Keeping in mind the above, the hydrotalcite structure solid of stage (1.1) is therefore, generally obtained from an aqueous solution containing magnesium nitrate and alumina nitrate with an advantageous Mg/Al molar ratio ranging between 1.6 and 3.8.

In the specific context of catalyst preparation possessing a hydrotalcite structure with a Mg/Al molar ratio specifically between 2.5 and 3.8, the hydrotalcite structure solid of stage (1.1) shows a Mg/Al ratio between 2.5 and 3.8. In this particular case, the Mg/Al ratio in the aqueous solution ranges between 2.5 and 3.8 preferably between 2.6 and 3.2; and, even more advantageously between 2.8 and 3.1. Thus this Mg/Al ratio could, for instance, be equal to 3.

By adding a base to the medium, especially NaOH, the pH value of the solution is then adjusted to a value preferably between 8 and 10. This. in this case, gives us a coprecipitation of magnesium and alumina salts. One then obtains a hydrotalcite structure solid in an aqueous suspension form.

It is preferable that the solid obtained is then isolated from the medium, for instance, like by filtration. The filtration stage is advantageously followed by a wet cleaning stage and a drying stage.

Moreover it must be noted that in order to avoid the presence of divalent carbonate anions within the solid obtained, the stage (1.1) of creating the hydrotalcite structure compound is generally advantageously carried out in atmosphere devoid of CO2, for instance under nitrogeneous atmosphere.

The stage (1.2) of exchange by fluoride anions is on the other hand usually carried out by dispersion of the solid obtained at the end of stage (1.1) in an aqueous solution containing fluoride anions with a concentration preferably between 0.05 and 0.5 mol/l.

This solution is advantageously an aqueous solution including at least one fluoride salt easily soluble in water or preferably in a solution of potassium, ammonium, sodium, magnesium and/or cesium fluoride. In order to introduce an optimum of fluoride ions into the structure, the fluoride ion solution used advantageously is also free of carbonate ions.

The anionic exchange reaction is a fairly quick reaction. It is usually carried out for a time period of 10 minutes to an hour and preferably for a time period of 20 to 30 minutes. Advantageously it is carried out under agitation.

Preferably, the solid obtained at the end of stage (1.2) is then subjected to filtration generally followed by drying. This operation is preferably undertaken in an atmosphere free of CO2, for instance under nitrogen atmosphere.

A second preparation method of a solid basic catalyst possessing a hydrotalcite structure and integrating fluoride anions as compensation anions, useful according to the invention, is characterised by stages which:

(11.1) Prepare mixed magnesium and aluminum oxide by hot-process carbonate removal of a carbonatised hydrotalcite structure solid.

(11.2) Hydrate the mixed oxide of stage (11.1) in the presence of fluoride ions.

The mixed magnesium and aluminum oxide obtained at stage (11.1) is a solid possessing a structure called 'HDT' defined above and belongs to the oxide type described in the Journal of Catalysis, volume 173, pages 115–121 (1998). The mixed oxide obtained at stage (11.1) is generally characterised by a Mg/Al molar ratio ranging from 1.6 to 3.8.

In the specific context of catalyst preparation possessing a hydrotalcite structure with a Mg/Al molar ratio specifically between 2.5 and 3.8, the mixed oxide of stage (11.1) is characterised specifically by a Mg/Al ratio ranging between 2.5 and 3.8, preferably between 2.6 and 3.2 and most advantageously between 2.8 and 3.1. The ratio especially preferable would be 3.

The carbonated hydrotalcite structure solid used in the carbonate removal stage can be prepared according to a method described by Reichle et al. in the Journal of Catalysis, volume 94, pages 547–557 (1985).

The removal of carbonates forming a mixed oxide is generally carried out by calcining and advantageously at a temperature of 400° to 600° C.

In order to avoid recarbonation of the solid obtained, the mixed oxide obtained at the end of stage (11.1) is usually cooled with nitrogen in the absence of CO2.

Stage (11.2) wherein the mixed oxide is hydrated reconstitutes the hydrotalcite structure. Herein, it must be noted that this structure's reconstruction phenomenon from the oxide is a relatively slow process, limited especially by the diffusion speed of water within the solid. Therefore, the hydration stage (11.2) is often a lengthy stage taking usually 5 to 48 hours.

This hydration stage is moreover conducted specifically in the presence of fluoride ions. It is therefore generally carried out by dispersion of the solid obtained at the end of stage (11.1) in an aqueous solution containing an optimum of fluoride ions, advantageously an aqueous solution of potassium, ammonium. sodium, magnesium and/or cesium fluoride, at an advantageous concentration ranging from 0.05 to 0.5 mol/l. in such a manner as to introduce an optimum of fluoride ions within the structure. The fluoride ion solution used is preferably free of carbonate ions. Moreover, this stage is carried out under agitation.

Preferably the solid obtained at the end of stage (11.2) goes through a filtration stage which is usually followed by drying. These stages are conducted; it is preferable, in a nitrogenous atmosphere free of CO2.

The objective and the advantages of the present invention will be clearer with the examples illustrated here below.

EXAMPLE 1

How to Prepare an 'HDT-F' Catalyst Useful According to the Invention

*How to Prepare a Carbonatised Hydrotalcite Structure of a Solid.

An aqueous solution of 0.2805 litre with a 0.2808 mole of Mg (NO3) 2, 6H2O and 0.093 mole of Al (NO3) 3, 9H2O (molar ratio Mg/Al=3) has been added to a second aqueous solution of 0.2805 litre containing 0.6562 mole of NaOH and 0.1687 mole of Na2CO3. Adding took 3 hours.

The suspension obtained was heated to 338 K for 16 hours. The precipitate then obtained was filtered, washed with warm distilled water until the filtration water pH was equal to 7. The carbonatized hydrotalcite was then dried in a heat/steaming chamber at 353K during 15 hours.

*How to Form a Mixed Magnesium and Aluminum Oxide

The carbonatized hydrotalcite obtained at the end of the drying stage was given calcining heat treatment under airflow with an increase in temperature from 25° C. to 450° C. in order to remove carbonates from the hydrotalcite and to form a mixed oxide of HDT structure. The mixed oxide has then been cooled under nitrogen to avoid recarbonation.

*How to Introduce Fluoride Ions

After cooling, a 1 g masse of mixed oxide was obtained and was suspended in an aqueous solution of potassium fluoride at 0.1 mol/l, obtained by dissolution of 0.581 g of KF in 100 ml of deionised and decarbonatised water.

The suspension obtained was agitated during 24 hours under a nitrogen bed in order to obtain a hydrotalcite structure integrating fluoride ions.

The solid obtained has then been filtered under nitrogenous conditions, washed with 0.4 litres of deionised and decarbonatized water and dried under vacuum at 80° C. In fine 1.38 g of solid was obtained.

EXAMPLE 2

Using Catalyst 'HDT-F' for the Basic Catalysis of Knoevenagel Condensation

The catalysis obtained in the first example was utilises to catalyse Knoevenagel reaction condensation by global budget/balance:

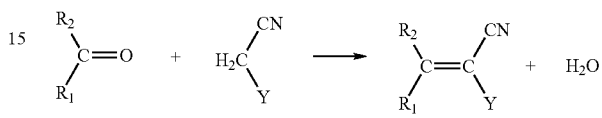

The table below groups the results observed for different kinds of compounds

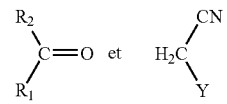

The corresponding reactions (a) to (p) have been achieved through reactions, under agitation and in 5 ml of solvent (dimethylformamide(ine?) DMF or acetonitril MeCN), of 1 millimole of carbonyl compound and 1 millimole of activated methanol, in the presence of 0.0035 g of 'HDT-F' catalyst prepared in example 1.

In each case, the progress of the reaction was followed by chromatography on a plate. At the end of the reaction the catalyst was filtered, the filtrate was washed with water and the product was extracted by sodium sulphate and concentrated under low pressure.

The indicated yield was calculated on the basis of NMR spectra observed at the final medium, on the basis of R1R2C=O ketonic compounds quantity consumed during the reaction.

TABLE 1

Knoevenagel Condensation Reaction

| | R1 | R2 | Y | Solvent | Reaction time | Yield |
|---|---|---|---|---|---|---|
| (a)[1] | Ph | H | CN | DMF | 15 min | 100 |
| (b)[2] | Ph | H | CO₂E | DMF | 2 h | 92 |
| (c)[1] | 3-OMeC₆H₄ | Me | CN | DMF | 15 min | 100 |
| (d)[2] | 3-OMeC₆H₄ | Me | CO₂Et | DMF | 2 h | 88 |
| (e)[1] | 4-NO₂C₆H₄ | H | CN | MeCN | 1.5 h | 100 |
| (f)[2] | 4-NO₂C₆H₄ | H | CO₂Et | MeCN | 1.5 h | 100 |
| (g)[1] | 4-OHC₆H₄ | H | CN | MeCN | 1.5 h | 100 |
| (h)[2] | 4-OHC₆H₄ | H | CO₂Et | MeCN | 1.5 h | 55 |
| (i)[1] | 2-OMeC₆H₄ | H | CN | DMF | 15 min | 100 |
| (j)[2] | 2-OMeC₆H₄ | H | CO₂Et | DMF | 2 h | 57 |
| (k)[1] | -cC₅H₁₀-[3] | | CN | DMF | 2 h | 100 |
| (l)[2] | -cC₅H₁₀-[3] | | CO₂Et | DMF | 2 h | 21 |
| (m)[1] | 4-ClC₆H₄ | H | CN | DMF | 15 min | 100 |
| (n)[2] | 4-ClC₆H₄ | H | CO₂Et | DMF | 2 h | 86 |
| (o)[1] | 3,4,5-OMeH₂ | H | CN | DMF | 15 min | 100 |
| (p)[2] | 3,4,5-OMeH₂ | H | CO₂Et | DMF | 2 h | 77 |

[1]reaction at 25° C.
[2]reaction at 60° C.
[3]the ketonic compound is cyclohexanone

EXAMPLE 3

Using the 'HDT-F' Catalyst for the Basic Catalysis of Michael's Reaction

The catalyst obtained in example 1 was utilised to catalyse Michael's reactions by global budget/balance:

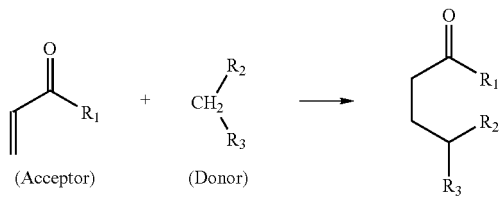

Table 2, hereunder, groups the results observed for different kinds of acceptors and donors.

The corresponding reactions (a) to (k) were achieved through reaction at a temperature of 25° C., under agitation and in 5 ml of dry acetonitril, 1 millimole of an acceptor like compound and 1 millimole of a donor like compound, in the presence of 0.1 g of 'HDT-F' catalyst prepared in example 1.

By way of indication, one has for some reactions indicated within brackets the yield and reaction time corresponding to the values obtained with other known catalysts (the indication ET is given before the values).

TABLE 2

Michael Reaction

| Réaction | Acceptor | Donor | Reaction time | Product | Yield |
|---|---|---|---|---|---|
| (a) | PhCH=CH−C(O)−Ph | nitromethane | 2 h [ET: 20 h[1]] | PhCH(CH2NO2)−CH2−C(O)−C6H5 | 90% [ET: 95%[1]] |
| (b) | PhCH=CH−C(O)−Ph | ethylcyano-acetate | 1.5 h | PhCH(C(CN)(CO2Et))−CH2−C(O)−Ph | 95% |
| (c) | PhCH=CH−C(O)−Ph | diéthyl-malonate | 2 h [Et: 8 h[1], 48 h[2], 6 h[3]] | PhCH(CH(CO2Et)2)−CH2−C(O)−Ph | 95% [Et: 95%[1], 96%[2], 75%[3]] |
| (d) | cyclohex-2-enone | diéthyl-malonate | 1.5 h | cyclohexanone-3-yl-CH(CO2Et)2 | 90% |
| (e) | cyclohex-2-enone | éthylcyano-acetate | 2 h | cyclohexanone-3-yl-CH(CN)(CO2Et) | 98% |
| (f) | cyclohex-2-enone | nitroéthane | 1.5 h [Et: 20 h[4], 2 h[5]] | cyclohexanone-3-yl-CH(CH3)(NO2) | 98% [Et: 93%[4], 100%[5]] |

TABLE 2-continued

Michael Reaction

| Réaction | Acceptor | Donor | Reaction time | Product | Yield |
|---|---|---|---|---|---|
| (g) | cyclohex-2-enone | diméthyl-malonate | 2 h | 3-(bis(methoxycarbonyl)methyl)cyclopentanone with $CO_2CH_3$, $CO_2CH_3$ | 98% |
| (h) | methyl vinyl ketone ($CH_3$) | acétyl-acetone | 2 h [ET: 96 h[2]] | $H_3COC$-CH($COCH_3$)-$CH_2CH_2COCH_3$ | 85% [ET: 79%[2]] |
| (i) | methyl vinyl ketone ($CH_3$) | diéthyl-malonate | 2 h [Et: 3 h[6], 72 h[2], 48 h[7], 4 h[8]] | $EtO_2C$-CH($CO_2Et$)-$CH_2CH_2COCH_3$ | 80% [Et: 78%[6], 70%[2], 90%[7], 90%[8]] |
| (j) | methyl vinyl ketone ($CH_3$) | éthylcyano-acetate | 2 h | $EtO_2C$-CH(CN)-$CH_2CH_2COCH_3$ | 70% |
| (k) | ethyl acrylate ($OCH_2CH_3$) | nitrométhane | 2 h [ET: 2 h[8]] | $O_2N$-$CH_2CH_2CH_2CO$-$OCH_2CH_3$ | 98% [ET: 77%[9]] |

[1]Calalyst Ba(OH)2 - Garcia et al., Synthesis, page 1037(1982)
[2]catalyst tBuOk on Xonoltile support - Laszlo et al., Tetrahedron Letters, Volume 26. page 264(1985).
[3]Calalyst hydrolalcile - (1 g for 2 millimoles of substrata)
[3]Calalyst Amberlyst A-27 - Ballini et al., Journal of Organic Chemistry, volume 61, page 3209(1996)
[4]CalalystKF on alumina - Bergabreiler et al., Journal of Organic Chemistry, volume 52 page 1601(1987)
[5]Catalyst Zeolite - Sreekumar et al., Tetrahedron Letters, volume 37, page 6557(1997)
[6]Catalyst NI(acoc)2 - Nelson et al., Journal of Organic Chemistry, volume 45, pages 1246–1249(1980)
[7]Catalyst Al2O3 - Ranu et al., Tetrahedron Letters, volume 32, pages 2811–2812(1992)

The invention claimed is:

1. A method of performing a Michael's addition comprising:
catalyzing a Michael's addition acceptor with a Michael's addition donor in the presence of a catalytically effect amount of hydrotalcite fluoride catalyst, wherein the reaction is performed under basic conditions.

2. The method of claim 1, wherein the Mg/Al molar ratio of the hydrotalcite fluoride catalyst is between 1.6 and 3.8.

3. The method of claim 1, wherein the hydrotalcite fluoride catalyst comprises at least 0.5% of fluoride ion mass.

4. The method of claim 1, wherein the hydrotalcite fluoride catalyst is a porous solid and the pore distribution radius is such that at least 50% have a mean diameter more than 2 nm.

5. The method of claim 1, wherein the hydrotalcite fluoride catalyst is used in the range of 0.01 g to 0.10 g per substrate millimole.

6. The method of claim 1, wherein the hydrotalcite fluoride catalyst is a porous solid and the pore distribution radius is such that at least 50% have a mean diameter more than 2 nm.

7. The method of claim 1, wherein the hydrotalcite fluoride catalyst is used in the range of 0.01 g to 0.10 g per substrate millimole.

* * * * *